(12) United States Patent
Kasama et al.

(10) Patent No.: US 6,852,311 B1
(45) Date of Patent: Feb. 8, 2005

(54) OPHTHALMIC OINTMENTS FOR TREATING INFECTIVE EYE DISEASE

(75) Inventors: Toshio Kasama, Toshima-ku (JP); Mitsuru Noto, Kurobe (JP); Susumu Oguro, Nakaniikawa-gun (JP); Isao Hanazome, Toyama (JP); Rena Tatekawa, Toyama (JP)

(73) Assignee: TOA Pharmaceutical Co., Ltd., Toyama (JP)

( * ) Notice: Subject to any disclaimer, the term of this patent is extended or adjusted under 35 U.S.C. 154(b) by 162 days.

(21) Appl. No.: 10/009,476

(22) PCT Filed: Jun. 28, 2000

(86) PCT No.: PCT/JP00/04226

§ 371 (c)(1),
(2), (4) Date: Dec. 11, 2001

(87) PCT Pub. No.: WO01/00226

PCT Pub. Date: Jan. 4, 2001

(30) Foreign Application Priority Data

Jun. 29, 1999 (JP) ............................................ 11-183345

(51) Int. Cl.⁷ .............................................. A61K 31/74
(52) U.S. Cl. ................................................... 424/78.04
(58) Field of Search ...................................... 424/78.04

(56) References Cited

FOREIGN PATENT DOCUMENTS

| EP | 342396 | 11/1989 |
|---|---|---|
| GB | 1537047 | 12/1978 |
| JP | 5441322 | 4/1979 |
| WO | 01/00226 | 6/2000 |

OTHER PUBLICATIONS

Hanna, et al "Delivery of Antibiotics to the Eye", Life Science, 1980.*
Tazawa, et al. "MRSA ocular infections" Database Medline on STN, 1992.
Eiferman, et al. "Methicillin–resistant *Staphylococcus aureus* corneal ulcers" Annals of Ophthalmology, 1991.
Smith "Treatment of experimental methicillin–resistant *Staphylococcus epidermidis* endophthalmitis with intravitreal vancomycin" Ophthalmology, 1986.
Hanna, et al. "Delivery of antibiotics to the Eye" Life Science, 1980.

* cited by examiner

*Primary Examiner*—Carlos A. Azpuru
(74) *Attorney, Agent, or Firm*—Crowell & Moring LLP

(57) ABSTRACT

Ophthalmic ointments for treating infective eye diseases which are particularly effective against infective eye diseases caused by methicillin-resistant *Staphylococcus aureus* (MRSA) or methicillin-resistant *Staphylococcus epidermidis* (MRSE) and contain as the active ingredient from 0.01 to 5.0% of vancomycin hydrochloride. Compared with intravenous administration, topical administration of these ophthalmic ointments is accompanied with no problem of the occurrence of side effects such as renal toxicity and thus enables the maintenance of a therapeutically effective concentration.

14 Claims, No Drawings

OPHTHALMIC OINTMENTS FOR TREATING INFECTIVE EYE DISEASE

BACKGROUND OF THE INVENTION

The present invention relates to ophthalmic ointments for treating infective eye diseases, and more particularly, to ophthalmic ointments for treating infective eye diseases caused by methicillin-resistant *Staphylococcus aureus* (MRSA) and methicillin-resistant *Staphylococcus epidermidis* (MRSE).

Development of antibiotics has been recognized to be a battle against relentlessly emerging resistant strains. In recent years, methicillin-resistant *Staphylococcus aureus* (MRSA) has been attracted significant attention as a new type of multiple drug-resistant bacteria which are responsible for infections in various medical fields. Also, there is growing concern about nosocomial MRSA infection as the number of reported cases of MRSA infection increases every year.

Gram-positive cocci, in particular staphylococci, are by far the most prevalent pathogens of infective eye diseases such as neonatal dacryocystitis, chronic dacryocystitis, conjunctivitis, hordeolum externum, blepharoadenoma, keratitis, corneal ulcer, blepharitis (including blepharitis marginalis), endophthalmitis, orbital cellulitis, Stevens-Johnson syndrome, orbital infections, and postoperative infections (including infections of buckling). Recently, it has been reported that the cases of eye infections caused by methicillin-resistant *Staphylococcus aureus* (MRSA) or methicillin-resistant *Staphylococcus epidermidis* (MRSA) are on the increase.

Furthermore, as an intraocular implant to the patients suffering from cataract become a popular procedure, postoperative MRSA or MRSE infections have become a matter of considerable concern.

Despite the growing concern over MRSA infection in the field of ophthalmology, no effective ophthalmic ointment has been proposed thus far as a therapeutic formulation of eye infections, especially those caused by MRSA.

Accordingly, it is an objective of the present invention to provide an ophthalmic ointment for treating infective eye diseases, and in particular, to provide an ophthalmic ointment for treating infective eye diseases caused by methicillin-resistant *Staphylococcus aureus* (MRSA) or methicillin-resistant *Staphylococcus epidermidis* (MRSE).

SUMMARY OF THE INVENTION

In view of the above-mentioned objective, one aspect of the present invention provides an ophthalmic ointment for treating infective eye diseases containing as an active ingredient from 0.01 to 5.0% of vancomycin hydrochloride.

Among others, the present invention is particularly directed to an ophthalmic ointment for treating infective eye diseases caused by MRSA or MRSE. More particularly, the present invention provides an ophthalmic ointment for treating infective eye diseases caused by methicillin-resistant *S. aureus* (MRSA) or methicillin-resistant *S. epidermidis* (MRSE) containing as an active ingredient from 0.01 to 5.0% of vancomycin hydrochloride.

As used herein, the term "infective eye diseases" refers to infective diseases including neonatal dacryocystitis, chronic dacryocystitis, conjunctivitis, hordeolum externum, blepharoadenoma, keratitis, corneal ulcer, blepharitis (including blepharitis marginalis), endophthalmitis, orbital cellulitis, Stevens-Johnson syndrome, orbital infections, and postoperative infections (including infections of buckling). Among others, the present invention is particularly directed to an ophthalmic ointment for treating or preventing of keratitis caused by MRSA (which may be referred to simply as "MRSA keratitis", hereinafter).

Thus, in a more specific embodiment, the present invention provides an ophthalmic ointment for treating MRSA keratitis containing as an active ingredient from 0.01 to 5.0% of vancomycin hydrochloride. In this regard, the present invention also provides an ophthalmic ointment for preventing MRSA keratitis containing as an active ingredient from 0.01 to 5.0% of vancomycin hydrochloride.

In the first place, the present inventors paid their attention to vancomycin hydrochloride, which is used as the agent of the first choice to treat MRSA infections, in an effort to provide the ophthalmic ointment for treating infective eye diseases in accordance with the present invention. No medical ointment containing vancomycin hydrochloride had been proposed until then and no one had ever conceived of the idea of using vancomycin hydrochloride in ophthalmic ointments.

At that point, the present inventors prepared an ophthalmic ointment containing vancomycin hydrochloride, as the agent of the first choice used to treat MRSA infections, applied the ointment to treat infective eye diseases, especially keratitis caused by MRSA, and discovered that the ointment exhibited excellent efficacy as a therapeutic formulation for treating such infective eye diseases.

Thus, the present invention is of absolute novelty in that it provides an ophthalmic ointment containing vancomycin hydrochloride, which no one has ever conceived of using in this form.

Vancomycin hydrochloride is little absorbed in the living body when orally administered and is hardly distributed to eyes tissue when intravenously injected. Therefore, maintaining the effective concentration of vancomycin in eye tissue requires a large quantity of solution for bolus intravenous injection, which may cause renal toxicity.

Accordingly, the ophthalmic ointment of the present invention, which is topically available of vancomycin hydrochloride, eliminates the above-mentioned disadvantages and provides a highly effective therapeutic formulation for treating infective eye diseases.

DETAILED DESCRIPTION OF THE PREFERRED EMBODIMENTS

In an ophthalmic ointment of the present invention containing vancomycin hydrochloride as an active ingredient, the content (i.e., concentration) of vancomycin hydrochloride is from 0.01 to 5.0%, preferably from 0.1 to 3.0%, more preferably from 0.3 to 1.0%, based on the amount of ophthalmic ointment preparation.

In the course of the study, the present inventors applied the ophthalmic ointment containing vancomycin hydrochloride at a concentration of 0.3% or 1.0%, to corneas of rabbits suffering MRSA keratitis and discovered that the ointment was effective not only in preventing keratitis caused by MRSA keratitis but also in curing the disease.

A preferred ointment base used to prepare the ophthalmic ointment of the present invention may be one that has been used in conventional ophthalmic ointments. In particular, the preferred base may be liquid paraffin, white petrolatum, purified lanolin, gelation hydrocarbon, polyethylene glycol, hydrophilic ointment base, white ointment base, absorptive ointment base, Macrogol (Trade Name) ointment base, simple ointment base, and the like.

The ophthalmic ointment of the present invention may contain further conventional excipients other than the ointment base in the range of without affecting the intended functions and stability of vancomycin hydrochloride to be contained. Examples of such excipients include antiseptics such as parahydroxybenzoate, chlorobutanol, benzalkonium chloride and the like; surfactants such as polysorbate 80, polyoxyl 40 stearate, polyoxyethylene hydrogenated castor oil and the like; stabilizers such as sodium edetate, citric acid, and salts thereof; alcohols such as glycerol, lanolin alcohol, cetanol and the like; esters such as isopropyl myristate, ethyl linoleate and the like; and oils such as olive oil and triglycerides of middle-chained fatty acids.

The ophthalmic ointment of the present invention can be produced as follows: if necessary, antiseptics, surfactants, stabilizers, alcohols, esters or oils are blended with an ointment base such as liquid paraffin or white petrolatum placed in a mortar or a mixing machine for ointment to form a mixture. This is followed by addition of vancomycin hydrochloride, and the resulting mixture is mixed until uniform and kneaded to form the ophthalmic ointment. The ointment thus prepared is filled into a bottle or tube for ointment to obtain the ophthalmic ointment containing vancomycin hydrochloride of the present invention.

The ophthalmic ointment containing vancomycin hydrochloride of the present invention obtained in the above-described manner is efficacious against infective eye diseases including neonatal dacryocystitis, chronic dacryocystitis, conjunctivitis, hordeolum externum, blepharoadenoma, keratitis, corneal ulcer, blepharitis (including blepharitis marginalis), endophthalmitis, orbital cellulitis, Stevens-Johnson syndrome, orbital infection, and postoperative infections (including infections of buckling).

The ophthalmic ointment of the present invention for treating infective eye diseases is particularly effective against those infective eye diseases caused by MRSA or MRSE. Among others, the ophthalmic ointment of the present invention is particularly effective for treating or preventing of keratitis caused by MRSA.

EXAMPLES

The present invention will now be described in detail with reference to specific examples, but it is to be noted that the present invention is not limited by these Examples in any way.

Example 1

20 g of liquid paraffin and 79 g of white petrolatum were placed in a mortar and were mixed and kneaded until uniform. This was followed by addition of 1 g of vancomycin hydrochloride and the resulting mixture was thoroughly kneaded to form a homogenous ophthalmic ointment containing 1 g of vancomycin hydrochloride.

Example 2

15 g of liquid paraffin and 84 g of white petrolatum were placed in a mortar and were mixed and kneaded until uniform. This was followed by addition of 1 g of vancomycin hydrochloride and the resulting mixture was thoroughly kneaded to form a homogenous ophthalmic ointment containing 1% of vancomycin hydrochloride.

Example 3

20 g of liquid paraffin and 79.7 g of white petrolatum were placed in a mortar and were mixed and kneaded until uniform. This was followed by addition of 0.3 g of vancomycin hydrochloride and the resulting mixture was thoroughly kneaded to form a homogenous ophthalmic ointment containing 0.3% of vancomycin hydrochloride.

Example 4

15 g of liquid paraffin and 84.9 g of white petrolatum were placed in a mortar and were mixed and kneaded until uniform. This was followed by addition of 0.1 g of vancomycin hydrochloride and the resulting mixture was thoroughly kneaded to form a homogenous ophthalmic ointment containing 0.1% of vancomycin hydrochloride.

Example 5

20 g of liquid paraffin and 79.97 g of white petrolatum were placed in a mortar and were mixed and kneaded until uniform. This was followed by addition of 0.03 g of vancomycin hydrochloride and the resulting mixture was thoroughly kneaded to form a homogenous ophthalmic ointment containing 0.03% of vancomycin hydrochloride.

Example 6

15 g of liquid paraffin and 82 g of white petrolatum were placed in a mortar and were mixed and kneaded until uniform. This was followed by addition of 3 g of vancomycin hydrochloride and the resulting mixture was thoroughly kneaded to form a homogenous ophthalmic ointment containing 3% of vancomycin hydrochloride.

Example 7

15 g of liquid paraffin and 80 g of white petrolatum were placed in a mortar and were mixed and kneaded until uniform. This was followed by addition of 5 g of vancomycin hydrochloride and the resulting mixture was thoroughly kneaded to form a homogenous ophthalmic ointment containing 5% of vancomycin hydrochloride.

Example 8

Storage Stability Test

The storage stability of ophthalmic ointments containing vancomycin hydrochloride obtained in Examples mentioned above was tested.

Each of the ophthalmic ointments was filled in a plastic tube and was stored in a thermostatic bath kept at 25° C. or at 30° C. As a stability test, the remaining ratio of vancomycin hydrochloride was measured with the passage of time by high-performance liquid chromatography. In the 2 months stability tests at 25° C. or at 30° C., the ophthalmic ointments of the present invention each showed excellent stability.

The results are shown in Table 1 below.

TABLE 1

| Concentration of agents | Initial | Remaining Ratio of Vancomycin/HCl | | | |
|---|---|---|---|---|---|
| | | 25° C./ 1 month | 25° C./ 2 months | 30° C./ 1 month | 30° C./ 2 months |
| 0.1% | 100% | 98.3% | 97.7% | 97.0% | 96.4% |
| 0.3% | 100% | 98.5% | 97.1% | 97.4% | 96.0% |
| 1.0% | 100% | 98.7% | 97.1% | 97.7% | 96.3% |

As can be seen from the results above, the ophthalmic ointments of the present invention each showed excellent stability.

Example 9

Pharmacological Test

1. Methods

A group of four white rabbits, weighing about 2.5 kg, was used for each test. A solution of MRSA for inoculation was prepared by taking the bacteria of MRSA cultured on blood agar with a loop and suspending them in saline (1 loop/1 ml). In accordance with a method described by Kondo et al (*Jpn. Rev. Clin. Opthalmol.*, 75(1981): 1421), the bacteria were inoculated onto each cornea in 17 spots by injecting the MRSA suspension using a tuberculin syringe having 27 G needle. Subsequently, 0.1 ml of the bacterial suspension were applied to both eyes. The ointment containing vancomycin hydrochloride of the present invention was then applied to the right eyes whereas only the base of the ointment was applied to the left eyes. The ointment and the base were applied 5 times a day for 2 days. The corneas were observed 48 hours after the inoculation.

Four concentrations of vancomycin hydrochloride, namely 0.03%, 0.1%, 0.3% and 1%, were used.

2. Results

In the eyes (left) applied only the base, the formation of abscess-like circular infiltration and strong iritis with fibrin at each needling positions were observed and significant eye mucus suffering from keratitis caused by MRSA was also observed.

In contrast, keratitis was completely prevented in the eyes to which the ointment containing 1.0% or 0.3% of vancomycin hydrochloride was applied (i.e., right eyes).

Further, punctate infiltration was observed only in one or two of the inoculation spots in each of the eyes to which the ointment containing 0.1% of vancomycin hydrochloride (i.e., right eyes) was applied whereas many punctate infiltration as well as partially orbicular infiltration were observed in the eyes to which the ointment with 0.03% of vancomycin hydrochloride (i.e., right eyes) was applied.

In view of the results above, it can be concluded that the ophthalmic ointment of the present invention containing 0.3% or more of vancomycin hydrochloride is capable of completely preventing MRSA keratitis and the ointment may be effective against MRSA keratitis even when the amount of vancomycin hydrochloride is less than 0.3%.

It should be noted that an ophthalmic ointment tends to remain in a conjunctival sac for a prolonged period of time while releasing drug in a sustained manner and the ophthalmic ointment of the present invention is considerably more effective as compared to when vancomycin is applied through dropping since it is designed to maintain the concentration of vancomycin in eye tissue higher than the minimum inhibitory concentration (MIC) for a prolonged time.

Industrial Applicability

As has been described thus far, the present invention provides an ophthalmic ointment that is effective against MRSA infective eye diseases in the field of ophthalmology. Considering the fact that no effective therapeutic formulation has ever been proposed in this field, the possible impact of the present invention will be of considerable medical importance.

In particular, intravenous administration of vancomycin requires a large quantity of solution for bolus intravenous injection in order to maintain the effective concentration of vancomycin since vancomycin is hardly distributed to eye tissue. This may lead to various side effects including renal toxicity.

In contrast, the ophthalmic ointment of the present invention is provided in the form of a topical ophthalmic ointment, which no one has ever conceived of, and therefore is capable of avoiding the side effects while maintaining the effective concentration of vancomycin in eye tissue. Accordingly, the ophthalmic ointment of the present invention can be used as a highly effective therapeutic formulation in treating infective eye diseases.

What is claimed is:

1. An ophthalmic ointment for treating infective eye diseases, containing as an active ingredient from 0.01 to 5.0% of vancomycin hydrochloride.

2. An ophthalmic ointment as claimed in claim 1, wherein said eye diseases are caused by methicillin-resistant *Staphylococcus aureus* (MRSA).

3. An ophthalmic ointment as claimed in claim 1, wherein said eye diseases are caused by methicillin-resistant *Staphylococcus epidermidis* (MRSE).

4. An ophthalmic ointment as claimed in claim 2, wherein said infective eye disease is keratitis.

5. An ophthalmic ointment as claimed in claim 3, wherein said infective eye disease is keratitis.

6. An ophthalmic ointment as claimed in claim 1, wherein said vancomycin hydrochloride is present in an amount of from 0.1 to 3.0%.

7. An ophthalmic ointment as claimed in claim 6, wherein said vancomycin hydrochloride is present in an amount of from 0.3 to 1.0%.

8. An ophthalmic ointment as claimed in claim 1, further comprising a member of the group consisting of liquid paraffin, white petrolatum, purified lanolin, gelation hydrocarbon, a polyethylene glycol, hydrophilic ointment base, white ointment base, simple ointment base, and mixtures thereof.

9. An ophthalmic ointment as claimed in claim 8, further comprising an excipient selected from the group consisting of antiseptics, surfactants, stabilizers, alcohols, esters, oils, and mixtures thereof.

10. An ophthalmic ointment as claimed in claim 9, said antiseptic is selected from the group consisting of parahydroxybenzoate, chlorobutanol, and benzalkonium chloride, said surfactant is selected from the group consisting of polysorbate 80, polyoxyl 40 stearate, and polyoxyethylene hydrogenated castor oil, said stabilizer is selected from the group consisting of sodium edetate, citric acid, and salts thereof, said alcohol is selected from the group consisting of glycerol, lanolin alcohol, and cetanol, said ester is selected from the group consisting of isopropyl myristate, and ethyl linoleate, and said oil is selected from the group consisting of olive oil and triglycerides of middle-chained fatty acids.

11. A method of treating infective eye diseases comprising topically administering an effective amount of the ophthalmic ointment of claim 1.

12. An ophthalmic ointment as claimed in claim 8, wherein said member is a mixture of polyethylene glycols known as Macrogol ointment base.

13. An ophthalmic ointment as claimed in claim 12, further comprising an excipient selected from the group consisting of antiseptics, surfactants, stabilizers, alcohols, esters, oils, and mixtures thereof.

14. An ophthalmic ointment as claimed in claim 13, said antiseptic is selected from the group consisting of parahydroxybenzoate, chlorobutanol, and benzalkonium chloride, said surfactant is selected from the group consisting of polysorbate 80, polyoxyl 40 stearate, and polyoxyethylene hydrogenated castor oil, said stabilizer is selected from the group consisting of sodium edetate, citric acid, and salts thereof, said alcohol is selected from the group consisting of glycerol, lanolin alcohol, and cetanol, said ester is selected from the group consisting of isopropyl myristate, and ethyl linoleate, and said oil is selected from the group consisting of olive oil and triglycerides of middle-chained fatty acids.

\* \* \* \* \*